United States Patent
Lau et al.

(10) Patent No.: US 11,723,713 B2
(45) Date of Patent: Aug. 15, 2023

(54) ELECTROSURGICAL BLADE WITH MINIMALLY EXPOSED EDGE, ALTERNATIVE TO COATED BLADE

(71) Applicant: Medtronic Advanced Energy LLC, Minneapolis, MN (US)

(72) Inventors: Nathaniel R. Lau, Dover, NH (US); Christopher Barden, Acton, MA (US); Jessica Sacks, Lynnfield, MA (US); William X. Siopes, Tyngsboro, MA (US)

(73) Assignee: MEDTRONIC ADVANCED ENERGY LLC, Minneapolis, MN (US)

( * ) Notice: Subject to any disclaimer, the term of this patent is extended or adjusted under 35 U.S.C. 154(b) by 649 days.

(21) Appl. No.: 15/841,790

(22) Filed: Dec. 14, 2017

(65) Prior Publication Data
US 2018/0168717 A1  Jun. 21, 2018

Related U.S. Application Data

(60) Provisional application No. 62/434,753, filed on Dec. 15, 2016.

(51) Int. Cl.
*A61B 18/14* (2006.01)
*A61B 18/18* (2006.01)
*A61B 18/00* (2006.01)
*A61B 18/12* (2006.01)

(52) U.S. Cl.
CPC .............. *A61B 18/14* (2013.01); *A61B 18/18* (2013.01); *A61B 2018/00077* (2013.01); *A61B 2018/00083* (2013.01); *A61B 2018/00148* (2013.01); *A61B 2018/00601* (2013.01); *A61B 2018/00607* (2013.01); *A61B 2018/1253* (2013.01); *A61B 2018/1412* (2013.01)

(58) Field of Classification Search
CPC .. A61B 2018/1412; A61B 2018/00601; A61B 2018/00607
See application file for complete search history.

(56) References Cited

U.S. PATENT DOCUMENTS

| | | | |
|---|---|---|---|
| 3,987,795 A * | 10/1976 | Morrison | A61B 18/1402 606/50 |
| 4,248,231 A * | 2/1981 | Herczog | A61B 18/14 606/48 |
| 4,589,411 A * | 5/1986 | Friedman | A61B 18/1402 606/49 |
| 5,521,576 A | 5/1996 | Collins | |
| 5,713,895 A * | 2/1998 | Lontine | A61B 18/1402 606/41 |
| 6,086,586 A | 7/2000 | Hooven | |

(Continued)

FOREIGN PATENT DOCUMENTS

WO   WO-2014184544 A1 * 11/2014 ........... A61B 18/042

*Primary Examiner* — Jaymi E Della
(74) *Attorney, Agent, or Firm* — Patterson Thuente, P.A.

(57) ABSTRACT

A cutting element for an electrosurgical device. The cutting element includes an elongate non-conductive body having a first face opposite a second face, the first face and the second face defining an edge there between. A conductive element is disposed only along the edge, the conductive element being configured to cut tissue with monopolar radiofrequency energy.

16 Claims, 3 Drawing Sheets

(56) References Cited

U.S. PATENT DOCUMENTS

| | | | | |
|---|---|---|---|---|
| 6,126,656 | A * | 10/2000 | Billings | A61B 18/1402 606/45 |
| 6,610,057 | B1 * | 8/2003 | Ellman | A61B 18/1402 606/49 |
| 9,037,226 | B2 | 5/2015 | Hacker et al. | |
| 2004/0049183 | A1 * | 3/2004 | Ellman | A61B 18/1485 604/35 |
| 2006/0047280 | A1 * | 3/2006 | Goble | A61B 18/14 606/48 |
| 2007/0005057 | A1 * | 1/2007 | Heim | A61B 18/1402 606/41 |
| 2008/0027428 | A1 * | 1/2008 | Palanker | A61B 18/1402 606/45 |
| 2008/0058821 | A1 * | 3/2008 | Maurer | A61B 18/1402 606/50 |
| 2009/0227885 | A1 | 9/2009 | Lowery et al. | |
| 2010/0022950 | A1 | 1/2010 | Anderson et al. | |
| 2011/0190766 | A1 * | 8/2011 | Morris | B28B 1/24 606/41 |
| 2012/0150165 | A1 * | 6/2012 | Conley | A61B 18/1482 606/33 |
| 2013/0060249 | A1 * | 3/2013 | Maeda | A61B 18/1482 606/42 |
| 2016/0051313 | A1 * | 2/2016 | Canady | A61B 18/042 606/39 |
| 2016/0120589 | A1 | 5/2016 | Smith et al. | |
| 2016/0213422 | A1 * | 7/2016 | Ineson | A61B 18/1402 |
| 2016/0324576 | A1 * | 11/2016 | Ebbutt | A61B 18/1815 |

\* cited by examiner

ELECTROSURGICAL BLADE WITH MINIMALLY EXPOSED EDGE, ALTERNATIVE TO COATED BLADE

CROSS-REFERENCE TO RELATED APPLICATION

This application is related to and claims priority to U.S. Provisional Patent Application Ser. No. 62/434,753, filed Dec. 15, 2016, entitled ELECTROSURGICAL BLADE WITH MINIMALLY EXPOSED EDGE, ALTERNATIVE TO COATED BLADE, the entirety of which is incorporated herein by reference.

STATEMENT REGARDING FEDERALLY SPONSORED RESEARCH OR DEVELOPMENT n/a

TECHNICAL FIELD

This present invention relates to electrosurgical devices, and in particular, monopolar radiofrequency electrosurgical devices.

BACKGROUND

Monopolar electrosurgical devices are surgical devices that are configured to dissect tissue with radiofrequency energy as opposed to dissection of tissue with a traditional scalpel. One of the main benefits of such devices are precision dissection on par with that of scalpel while providing the bleeding control capability of traditional electrosurgery with minimal thermal injury to collateral tissue. This results in a highly efficient cut that requires less power to operate and improves patient outcomes by reducing collateral tissue damage.

Currently, some monopolar electrosurgical devices are manufactured by including a conductive substrate, such as an electrode, that is coated with a glass-based insulator material. In some devices, the resulting cutting tip includes minimally exposed conductive edge that is in the range of 1 to 100 microns in width. Therefore, approximately greater than 99% of the cutting tip is insulated and less than 1% is exposed. This minimally exposed edge enables the focused energy to be delivered only at the exposed edge, while the remainder of the tip is insulated and kept at a relatively low temperature. The end result is precision cutting with minimal collateral damage. However, this method of manufacture requires an expensive glass-coating process, potential for manufacturing efficiency, and reduction in reliance on highly custom materials.

SUMMARY

Some embodiments advantageously provide for a cutting element for an electrosurgical device. The cutting element includes an elongate non-conductive body having a first face opposite a second face, the first face and the second face defining an edge there between. A conductive element is disposed only along the edge, the conductive element being configured to cut tissue with monopolar radiofrequency energy.

In another aspect of this embodiment, the edge is a chamfered edge.

In another aspect of this embodiment, the first face and the second face are substantially flat.

In another aspect of this embodiment, the conductive element is composed of one from the group consisting of silver alloy and gold alloy.

In another aspect of this embodiment, the elongate non-conductive body is composed of Zirconium toughened Alumina.

In another aspect of this embodiment, the elongate non-conductive body includes a proximal end and a distal end, and wherein the distal end is curved.

In another aspect of this embodiment, the conductive element is etched onto the elongate non-conductive body.

In another aspect of this embodiment, the elongate non-conductive body defines a perimeter and wherein the conductive element is disposed around the perimeter.

In another aspect of this embodiment, the elongate non-conductive body includes a soldered conductor on the first face, the conductor being configured to electrically couple the conductive element to a shaft of the electrosurgical device.

In another aspect of this embodiment, the cutting element is configured to be coupled to an elongate shaft, and wherein the elongate shaft is coupled to a handle of the electrosurgical device.

In another embodiment, a cutting element for an electrosurgical device includes an elongate non-conductive body having a first face opposite a second face and defining a major longitudinal axis, the first face and the second face defining a double chamfered edge there between. A conductive element is disposed only along the double chamfered edge, the conductive element being substantially perpendicular to the major elongate axis, the conductive element being configured to cut tissue with monopolar radiofrequency energy.

In another aspect of this embodiment, the conductive element is one from the group consisting of gold alloy ink and silver alloy ink printed on the double chamfered edge.

In another aspect of this embodiment, the first face and the second face are substantially flat.

In another aspect of this embodiment, the elongate non-conductive body is composed of Zirconium toughened Alumina.

In another aspect of this embodiment, the elongate non-conductive body includes a proximal end and a distal end, and wherein the distal end is curved.

In another aspect of this embodiment, the elongate non-conductive body defines a perimeter and wherein the conductive element is disposed around substantially the entirety of the perimeter.

In another aspect of this embodiment, the elongate non-conductive body includes a soldered conductor on the first face, the conductor being configured to electrically couple the conductive element to a shaft of the electrosurgical device.

In another aspect of this embodiment, the cutting element is configured to be coupled to an elongate shaft, and wherein the elongate shaft is coupled to a handle of the electrosurgical device.

In another aspect of this embodiment, the conductive element is disposed along a midpoint of a width of the conductive element.

In another embodiment, an electrosurgical device includes a handle. An elongate shaft extends from the handle, the elongate shaft defines a proximal end coupled to the handle and a distal end. A cutting element is coupled to the distal end of the shaft, the cutting element includes a flat and elongate non-conductive body having a first face opposite a second face and defines a major longitudinal axis, the first face and the second face define a double chamfered edge there between, the non-conductive body defines a proximal end coupled to the elongate shaft and an arcuate distal end. A conductive element composed of a silver alloy is printed only along the double chamfered edge, the conductive element being substantially perpendicular to the major elongate axis, the conductive element being configured to cut tissue with monopolar radiofrequency energy.

BRIEF DESCRIPTION OF THE DRAWINGS

A more complete understanding of embodiments described herein, and the attendant advantages and features thereof, will be more readily understood by reference to the following detailed description when considered in conjunction with the accompanying drawings wherein.

DETAILED DESCRIPTION

As used herein, relational terms, such as "first" and "second," "top" and "bottom," and the like, may be used solely to distinguish one entity or element from another entity or element without necessarily requiring or implying any physical or logical relationship or order between such entities or elements.

As used herein, relational terms, such as "first" and "second," "top" and "bottom," and the like, may be used solely to distinguish one entity or element from another entity or element without necessarily requiring or implying any physical or logical relationship or order between such entities or elements.

Figure 1:
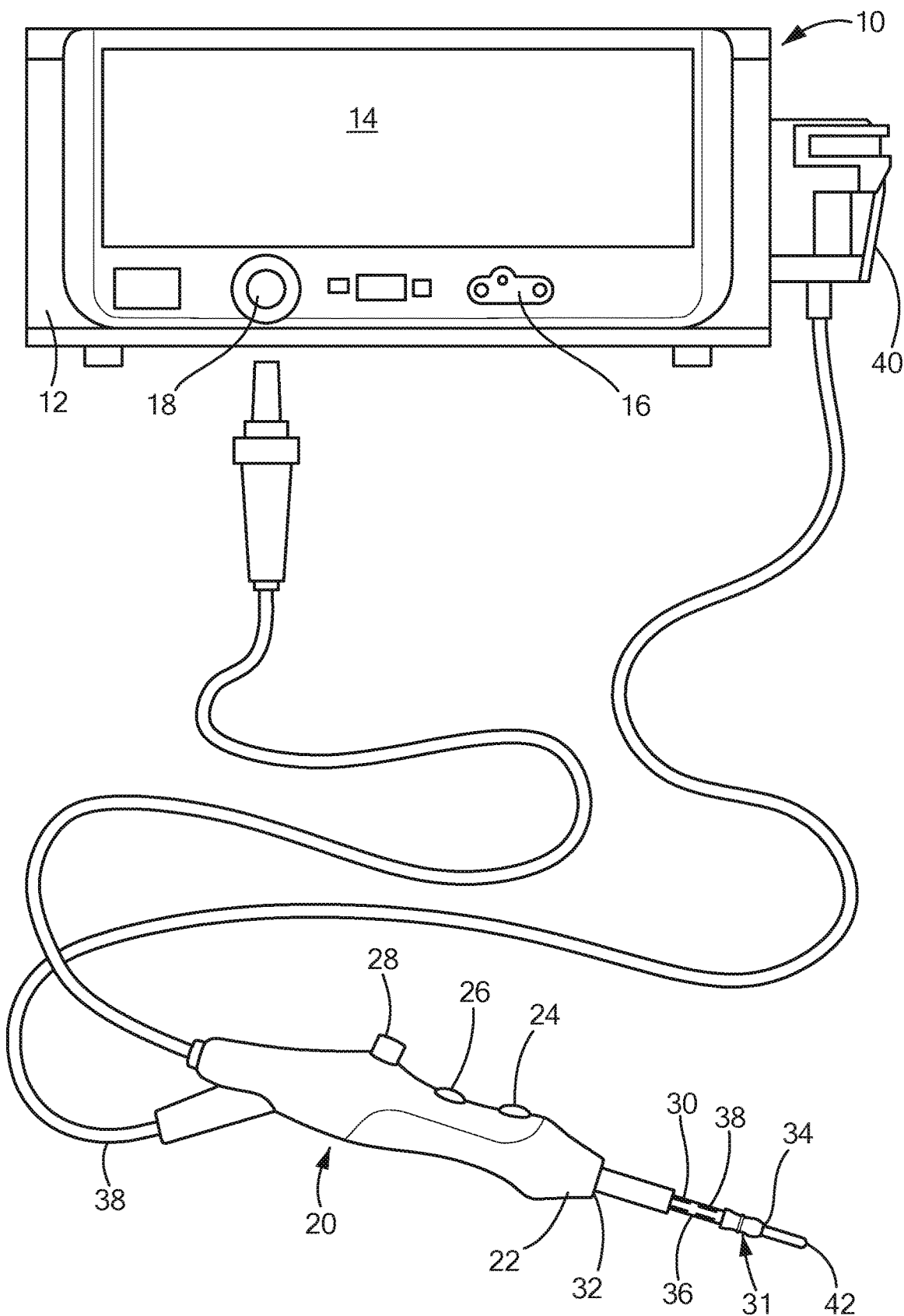
FIG. 1 is a system view of an electrosurgical unit and electrosurgical device constructed in accordance with the principles of the present application.

Referring now to the drawings in which like reference designators refer to like elements, there is shown in FIG. 1 and exemplary electrosurgical unit ("ESU") constructed in accordance with the principles of the present application and designated generally as "10." The ESU 10 may include a radiofrequency generator 12 configured to house and electrically couple the components and circuits of the ESU 10 and a touch actuated display 14 configured to receive energy requests from one or more electrosurgical hand pieces that electrically couple to the radiofrequency generator 12, display treatment progress and measurements, for example, impedance, and initiate and/or terminate the supply of radiofrequency energy and fluid with one or more electrosurgical hand pieces that may be electrically coupled to the ESU 10. In an exemplary configuration, the ESU 10 includes a first receptacle 16, which may be a 3-pin connector configured to receive and electrically couple with a bipolar electrosurgical hand piece (not shown) configured to deliver bipolar radiofrequency energy to tissue. The ESU 10 may further include a second receptacle 18, for example, a 7-pin receptacle, configured to receive and electrically couple with an electrosurgical hand piece 20 configured to deliver at least one of monopolar radiofrequency energy or a combination of bipolar radiofrequency energy and monopolar radiofrequency energy. Additional details about an exemplary ESU 10 of the present application may found in U.S. patent application Ser. No. 14/927,999, filed Oct. 30, 2015, entitled RF OUTPUT STAGE SWITCHING MECHANISM, the entirety of which is incorporated herein by reference. In other configurations, the ESU 10 may include a single receptacle configured to deliver one or both of monopolar and bipolar radiofrequency energy to which the bipolar electrosurgical hand piece or the electrosurgical hand piece 20 may couple with.

Continuing to refer to FIG. 1, the electrosurgical hand piece 20 the may include a handle 22 which couples to the second receptacle 18 and includes a first actuator 24 configured to initiate operation of the hand piece 20 in CUT mode, a second actuator 26 configured to initiate operation of the hand piece 20 in COAG mode, and a third actuator 28 configured to initiate operation of the hand piece 20 in TRANS mode. Although three actuators are shown which initiate various functions of the hand piece 20, it is contemplated that only the first actuator 24 may be included, or the first actuator 24 and the second actuator 26 may only be included. As described herein CUT mode operates the hand piece 20 to dissect and/or resect tissue; COAG mode operates the hand piece 20 to coagulate tissue for hemostasis; and TRANS mode operates the hand piece 20 to coagulate tissue while releasing a fluid.

Extending distally from the handle 22 may be an elongate shaft 30 defining a proximal end 32, a distal end 34, and a lumen 36 there between. The proximal end 32 of the shaft 30 may be coupled to the distal end of the handle 22. In an exemplary configuration, one or more conductors (not shown) may extend through the handle 22 and connect to the shaft 30 or extend through the lumen 36 toward the distal end 34 of the shaft 30 to electrically connect the ESU 10 with the hand piece 20 when the hand piece 20 is coupled to the second receptacle 18. Alternatively, the shaft 30 may be composed of an electrically conductive material, such as stainless steel, and may function as a conductor to transfer radiofrequency energy from the ESU 10 to the distal end 34 of the shaft 30. In one configuration the shaft 30 may be malleable such that it may be manipulated from a first configuration into a second configuration and optionally may be extendable and retractable by pulling or pushing on a finger grip 31. In an exemplary configuration, the shaft 30 may be covered with an insulating material such as heat shrink such that the interior of the shaft 30 may be conductive but the exterior of the shaft 30 may be insulated. In one configuration, a fluid conduit 38 may be disposed within the lumen 36 shaft 30 spanning from the proximal end 32 to the distal end 34. The fluid conduit 38 may be configured to transport fluid, such as saline from the ESU 10 having an integrated fluid source 40 or a separate fluid source 40 to the distal end 34 of the shaft 30. In an exemplary configuration, the fluid conduit 38 may be insulated from the shaft 30 such that fluid transported within the fluid conduit is not energized before it exits the distal end 34 of the shaft 30. In another configuration, the fluid conduit 38 is in electrical communication with the shaft 30 such that fluid exiting the distal end 34 of the shaft 30 is energized.

Figure 2:
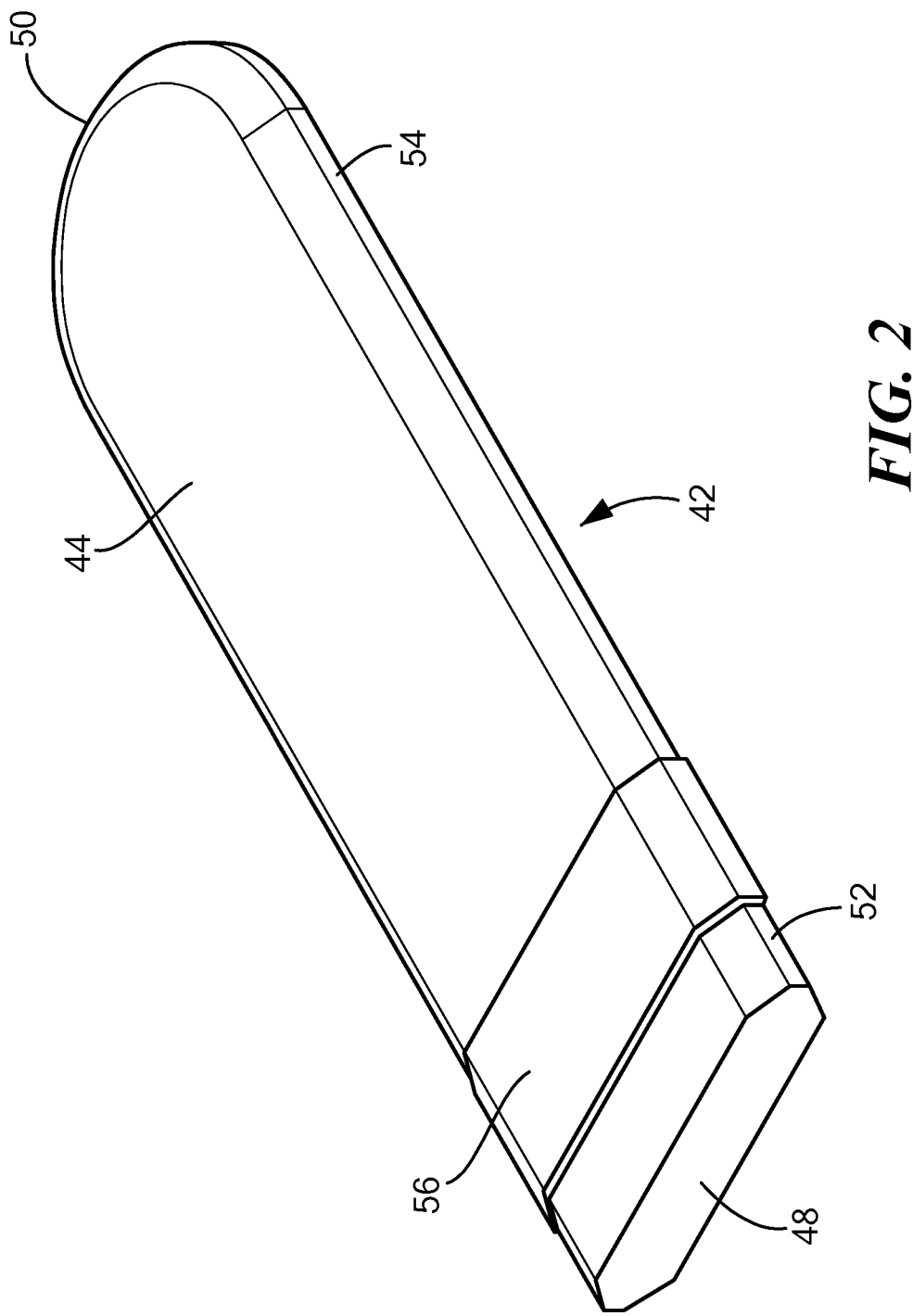
FIG. 2 is a perspective view of the cutting element of the electrosurgical device shown in FIG. 1.
Figure 3:
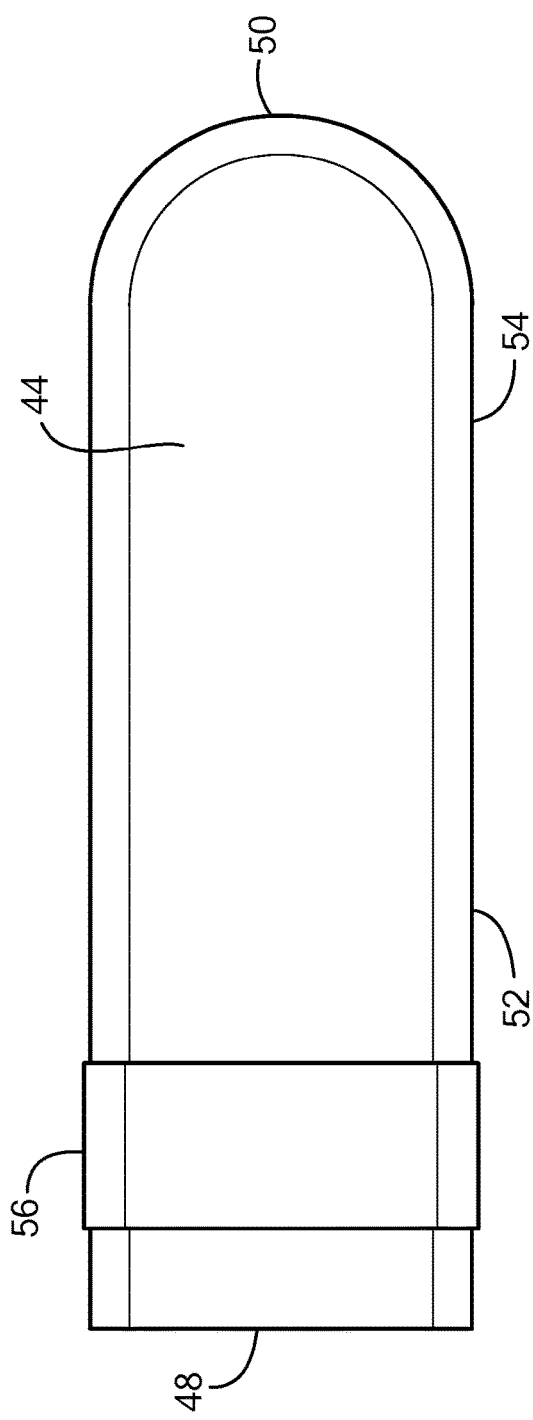
FIG. 3 is a side view of the cutting element shown in FIG. 2.

Now referring to FIGS. 1 and 2, extending from the distal end 34 of the shaft 30 may include a cutting element 42 configured to cut, coagulate, and/or coagulate tissue with a fluid with monopolar radiofrequency energy. In one configuration, the cutting element 42 may be composed of a non-conductive substrate such as ceramic, for example, aluminum oxide or Zirconium toughened Alumina. The cutting element 42 may be elongate in shape and may include a first face 44 opposite a second face 46 (shown in FIG. 4). In one configuration, for example, the configuration shown in FIG. 2, the first face 44 and the second face 46 may be flat and in another configuration the first face 44 and/or the second face 46 may define a curved surface, whether a concavity or convexity. The cutting element 42 may include a proximal end 48, which permanently or releasably couples with the distal end 34 of the shaft 30, and a distal end 50. For example, the proximal end 48 may be molded or soldered to the shaft 30, or alternatively, the proximal end 48 may snap-fit or include a bayoneted-type connection to releasably couple to the shaft 30. The distal end 50 may be curved, arcuate, flat, beveled, sharp or any number of configurations depending on the application. In an exemplary configuration, the cutting element 42 may define a length ("l") of 0.50", with a range in other embodiments from 0.25" to 2.0"; a width ("w") of 0.15", with a range in other embodiments from 0.10" to 0.70" and a thickness ("t") of 0.03", with a range in other embodiments from 0.01" to 0.07".

Figure 4:
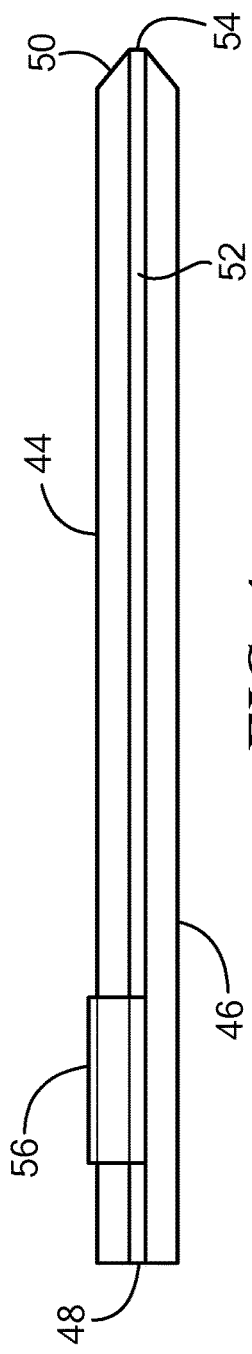
FIG. 4 is a top view of the cutting element shown in FIG. 3.
Figure 5:
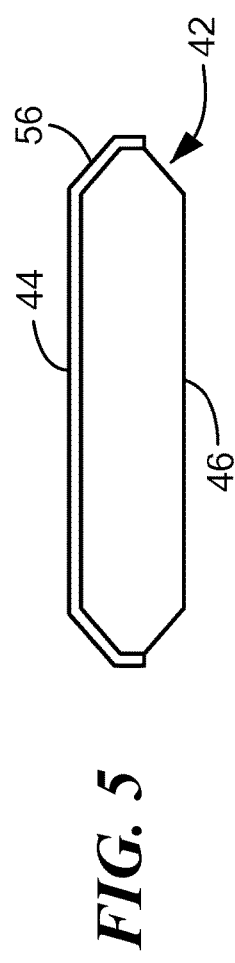
FIG. 5 is a bottom view of the cutting element shown in FIG. 4.

Referring now to FIGS. 2-5, the first face 44 and the second face 46 may cooperate to define an edge 52 along the perimeter of the cutting element 42. In particular, the first face 44 and the second face 46 may each taper in thickness as they extend toward the perimeter of the cutting element such the first face 44 and the second face 46 define a chamfered edge 52 around the perimeter of the cutting element 42. In other words, the first face 44 and the second face 46 may define a double chamfered edge as shown in FIG. 4. Alternatively, only one of the first face 44 and second face 46 may define a chambered edge, while the other is flat. The edge 52 may include a conductive element 54 deposited or otherwise printed on its surface. In particular, a trace material, such as silver alloy ink, gold ink, or other metallic or metal allow materials may be etched or otherwise deposited onto the surface of the of the cutting element 42 along only the edge 52. The conductive element 54 may completely or partially surround the cutting element 42. For example, the conductive element 54 may be disposed on one side of the cutting element 42 such that the edge 52 is only conductive on a single side of the cutting element; the conductive element 54 may be disposed only at the distal end of the cutting element 42 on the curved portion of the distal end 50; or the conductive element 54 may be disposed on the edge 50 around the entire perimeter of the cutting element 42. In one configuration, the conductive element 54 defines a flat and co-planar surface with the edge 52 and about the midpoint between the width of the face 44 and the second face 46. In an exemplary configuration, the edge 52 thickness, after etching on the conductive element 54 may be define a thickness of 0.006", with a range in other embodiments from 0.003" to 0.10". The conductive element 54 may be in electrical communication with the shaft 30, and therefore the ESU 10, by either directly coupling to the distal end 34 of the shaft 30 or by a separate conductor (not shown). For example, the cutting element 42 may further include a soldering strip 56 configured to electrically couple the cutting element 42 to the shaft 30. The soldering strip 56 may further be electrically coupled to the conductive element 54 such that radiofrequency energy may be directed from the ESU 10 to the cutting element 42. In an exemplary configuration, the soldering strip 56 is disposed on the first face 44 and not on the second face 46. In other configurations, the soldering strip surrounds the cutting element 42. The cutting element 42 may further include a port (not shown) proximate the proximal end 48 configured to release fluid from the fluid conduit 38 onto the cutting element 42. In such a configuration, the cutting element 42 may be configured to coagulate tissue while releasing a conductive fluid such as saline. In another configuration, one or more conductors (not shown) may be disposed within the cutting element 42 sandwiched between the first face 44 and the second face 46. The one or more conductors may be configured to provide a current pathway to the conductive element 54 should a section of the conductive element 54 break-off or otherwise erode during application of electrosurgical energy, which may create a short. For example, the one or more conductors may define a mesh-like configuration and may be coupled to various locations along the perimeter of the conductive element 54 to provide a back-up conductive pathway should a portion of the conductive element erode and disrupt the current pathway.

It will be appreciated by persons skilled in the art that the present embodiments are not limited to what has been particularly shown and described herein above. In addition, unless mention was made above to the contrary, it should be noted that all of the accompanying drawings are not to scale. A variety of modifications and variations are possible in light of the above teachings without departing from the scope of the following embodiments.

What is claimed is:

1. A cutting element for an electrosurgical device, comprising:
   a conductive shaft;
   an elongate non-conductive body defining a major longitudinal axis having a first face opposite a second face, the first face and the second face joining to define an edge;
   the elongate non-conductive body having a proximal end and a distal end opposite the proximal end, the distal end having a rounded portion;
   a conductive element that does not protrude from the edge and defines a flat and co-planar surface with the edge, the conductive element being disposed only along the edge, only along a midpoint of a width of the elongate non-conductive body, and only along the rounded portion of the distal end of the elongate non-conductive body, the conductive element being configured to cut tissue with monopolar radiofrequency energy; and
   the elongate non-conductive body includes a soldering strip disposed only on the first face and the edge, the soldering strip spanning an entire width of a proximal portion of the elongate non-conductive body transverse to the major longitudinal axis, the soldering strip being configured to electrically couple the conductive element to the conductive shaft of the electrosurgical device.

2. The cutting element of claim 1, wherein the edge is a chamfered edge.

3. The cutting element of claim 1, wherein the first face and the second face are flat.

4. The cutting element of claim 1, wherein the conductive element is composed of one from the group consisting of silver alloy and gold alloy.

5. The cutting element of claim 1, wherein the elongate non-conductive body is composed of zirconium toughened alumina (ZTA).

6. The cutting element of claim 1, wherein the distal end of the elongate non-conductive body is curved.

7. The cutting element of claim 1, wherein the conductive element is etched onto the elongate non-conductive body.

8. The cutting element of claim 7, wherein the elongate non-conductive body defines a perimeter and wherein the conductive element is disposed around the perimeter.

9. The electrosurgical device of claim 1, wherein the edge is a double chamfered edge and the double chamfered edge has a thickness of 0.006".

10. The electrosurgical device of claim 9, wherein the thickness of the conductive element and the double chamfered edge is between 0.003" and 0.10".

11. A cutting element for an electrosurgical device, comprising:
a conductive shaft;
an elongate non-conductive body having a first face opposite a second face and defining a major longitudinal axis, the first face and the second face joining to define a double chamfered edge;
the elongate non-conductive body having a proximal end and a distal end opposite the proximal end, the distal end having a rounded portion;
a conductive element that does not protrude from the double chamfered edge and defines a flat and co-planar surface with the double chamfered edge, the double chamfered edge being disposed only along a midpoint of a width of the elongate non-conductive body, the conductive element being disposed only along the double chamfered edge, only along a midpoint of the width of the elongate non-conductive body, and only along the rounded portion of the distal end of the elongate non-conductive body;
the conductive element being configured to cut tissue with monopolar radiofrequency energy; and
the elongate non-conductive body includes a soldering strip disposed only on the first face and the double chamfered edge, the soldering strip spanning an entire width of a proximal portion of the elongate non-conductive body and transverse to the major longitudinal axis, the soldering strip being configured to electrically couple the conductive element to the conductive shaft of the electrosurgical device.

12. The cutting element of claim 11, wherein the conductive element is one from the group consisting of gold alloy ink and silver alloy ink printed on the double chamfered edge.

13. The cutting element of claim 11, wherein the first face and the second face are flat.

14. The cutting element of claim 11, wherein the elongate non-conductive body is composed of ZTA.

15. The cutting element of claim 11, wherein the conductive shaft is composed of stainless steel.

16. An electrosurgical device, comprising:
a handle;
a conductive elongate shaft extending from the handle and defining a major longitudinal axis, the conductive elongate shaft defining a proximal end coupled to the handle and a distal end opposite the proximal end;
a cutting element coupled to the distal end of the conductive elongate shaft, the cutting element including:
a flat and elongate non-conductive body having a first face opposite a second face and defining a major longitudinal axis, the first face and the second face joining to define a double chamfered edge, the flat and elongate non-conductive body defining a proximal end coupled to the conductive elongate shaft and an arcuate distal end;
a conductive element that does not protrude from the double chamfered edge and defines a flat and co-planar surface with the double chamfered edge, the double chamfered edge being disposed only along a midpoint of a width of the elongate non-conductive body, the conductive element being disposed only along the double chamfered edge only along a midpoint of the width of the elongate non-conductive body and only along the arcuate distal end of the elongate non-conductive body, the conductive element being configured to cut tissue with monopolar radiofrequency energy; and
the elongate non-conductive body includes a soldering strip disposed only on the first face and the double chamfered edge, the soldering strip spanning an entire width of a proximal portion of the elongate non-conductive body transverse to the major longitudinal axis, the soldering strip being configured to electrically couple the conductive element to the conductive elongate shaft of the electrosurgical device.

* * * * *